(12) United States Patent
Ishiguro et al.

(10) Patent No.: US 8,417,413 B2
(45) Date of Patent: Apr. 9, 2013

(54) OXYGEN SENSOR CONTROL APPARATUS

(75) Inventors: Yasuhiro Ishiguro, Komaki (JP); Katsunori Yazawa, Kasugai (JP); Yuji Kimoto, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 0 days.

(21) Appl. No.: 13/415,531

(22) Filed: Mar. 8, 2012

(65) Prior Publication Data

US 2012/0232745 A1 Sep. 13, 2012

(30) Foreign Application Priority Data

Mar. 9, 2011 (JP) ................................. 2011-051801

(51) Int. Cl.
*G06F 19/00* (2011.01)
(52) U.S. Cl.
USPC ........ 701/33.1; 701/109; 701/30.8; 701/30.9; 702/104; 703/2; 73/1.06
(58) Field of Classification Search .................. 701/30.5, 701/30.8, 30.9, 31.1, 33.1, 99, 109; 702/104; 703/2; 73/1.06
See application file for complete search history.

(56) References Cited

U.S. PATENT DOCUMENTS

| | | | | |
|---|---|---|---|---|
| 4,592,325 A * | 6/1986 | Nakagawa | ..................... | 123/675 |
| 4,601,809 A * | 7/1986 | Kitahara | ........................ | 204/406 |
| 5,416,710 A * | 5/1995 | Kuroda et al. | ................ | 701/104 |
| 5,967,125 A * | 10/1999 | Morikawa | ..................... | 123/520 |
| 6,148,611 A * | 11/2000 | Sato | ................................. | 60/274 |
| 6,631,632 B2 * | 10/2003 | Matsubara et al. | ............. | 73/1.06 |
| 6,742,379 B2 * | 6/2004 | Matsubara et al. | ............. | 73/1.06 |
| 7,197,866 B2 * | 4/2007 | Cook et al. | ........................ | 60/285 |
| 7,243,487 B2 * | 7/2007 | Shouda et al. | ................... | 60/285 |
| 7,367,330 B2 | 5/2008 | Yoshidome | | |
| 8,001,765 B2 * | 8/2011 | Kawakita et al. | ............... | 60/276 |
| 2004/0040366 A1 * | 3/2004 | Matsubara et al. | ............. | 73/1.06 |
| 2010/0050602 A1 * | 3/2010 | Fujimoto | ......................... | 60/277 |
| 2011/0166816 A1 * | 7/2011 | Ishiguro et al. | ................ | 702/104 |

FOREIGN PATENT DOCUMENTS

JP 2007-32466 A 2/2007

OTHER PUBLICATIONS

Rheaume, J.M. Solid State Electrochemical Sensors for Nitrogen Oxide (NOx) Detection in Lean Exhaust Gases, Dissertation—University of California, Berkley, Spring 2010, pp. 1-165.*

* cited by examiner

*Primary Examiner* — Russell Frejd
(74) *Attorney, Agent, or Firm* — Sughrue Mion, PLLC (57) ABSTRACT

In an oxygen sensor control apparatus, after start of fuel cut, the weighted average Ipd of corrected values obtained by multiplying the output value of a mounted oxygen sensor by a correction coefficient Kp is obtained as a representative value Ipe, representing the corrected values in the fuel cut period (S19). In the case where the number of times the representative value Ipe is continuously judged not to fall outside a second range (S21: NO) and to fall outside a first range (S23: YES) reaches 10 (a first number of times) (S26: YES), a new correction coefficient Kp is computed (S27). In the case where the number of times the representative value Ipe is continuously judged to fall outside the second range (S21: YES) reaches 4 (a second number of times smaller than the first number of times) (S29: YES), a new correction coefficient Kp is computed (S30).

5 Claims, 5 Drawing Sheets

OXYGEN SENSOR CONTROL APPARATUS

BACKGROUND OF THE INVENTION

1. Field of the Invention

The present invention relates to an oxygen sensor control apparatus which detects oxygen concentration within exhaust gas by use of an oxygen sensor.

2. Description of the Related Art

Conventionally, an oxygen sensor has been disposed in an exhaust passage (exhaust pipe) of an internal combustion engine of an automobile or the like so as to detect the oxygen concentration of exhaust gas for the purpose of controlling the air-fuel ratio of the engine. Such an oxygen sensor includes, for example, a gas detection element which has at least one cell composed of an oxygen ion conductive zircona body and a pair of electrodes formed thereon. However, such an oxygen sensor has a problem. That is, the detection accuracy of the oxygen concentration changes because of variation in output characteristics among individual oxygen sensors and deterioration of each oxygen sensor with time. In order to solve such a problem, a technique has been proposed of performing ambient atmosphere correction; i.e., a technique of stopping supply of fuel to an internal combustion engine, calculating a correction coefficient when the exhaust passage is assumed to be substantially completely filled with ambient atmosphere, and calibrating (correcting) the relation between an output value of an oxygen sensor and oxygen concentration (see, for example, Patent Document 1).

[Patent Document 1] Japanese Patent Application Laid-Open (kokai) No. 2007-32466

3. Problems to be Solved by the Invention

However, even in a state in which the supply of fuel to the internal combustion engine is stopped (so-called "fuel cut"), the output value of the oxygen sensor fluctuates because it pulsates as a result of operation of the internal combustion engine, and noise is superimposed on the output thereof. In order to reduce the influence of such fluctuation, a method may be employed of determining a timing for calibration when the output value of the oxygen sensor deviates, by a predetermined amount or greater, from a reference value successively in a predetermined number (two or more) of fuel cut operations, and computing a correction coefficient at that timing. In the case where the oxygen sensor deteriorates with time, the accuracy in detection of oxygen concentration by the oxygen sensor deteriorates gradually. Therefore, after the output value of the oxygen sensor has gradually deviated from a predetermined range, a correction coefficient is computed upon performing a predetermined number of fuel cut operations, and the relation between the output value of the oxygen sensor and the oxygen concentration of exhaust gas is calibrated. The correction coefficient is not computed in a period during which the predetermined number of fuel cut operations are performed. However, since the output value of the oxygen sensor is close to the predetermined range, the oxygen concentration of exhaust gas flowing through the exhaust pipe can be detected relatively accurately.

Meanwhile, in the case where an oxygen sensor attached to an internal combustion engine is replaced with a new one, the output value of the new oxygen sensor may greatly deviate from the predetermined range due to a difference (variation attributable to an individual difference) in characteristics or a difference in degree of deterioration between the old and new oxygen sensors. Also, in the case where a correction coefficient calculated for the old oxygen sensor is stored, the oxygen concentration is calculated from that correction coefficient and the output value of the new oxygen sensor. Therefore, the accuracy in detecting the oxygen concentration of exhaust gas flowing through the exhaust pipe deteriorates. An operator who has changed the oxygen sensor may compute a correction coefficient for the new oxygen sensor so as to avoid the above-mentioned problem. However, such computation is troublesome for the operator. Since a control apparatus for controlling the oxygen sensor has a function of computing such a correction coefficient, it is desirable to compute such a correction coefficient by making use of that function. In view of the above, the control apparatus must calculate an optimal correction coefficient for the new oxygen sensor as soon as possible, and calibrate the relation between the output value of the oxygen sensor and the oxygen concentration of exhaust gas. However, the correction coefficient is not computed unless a predetermined number of fuel cut operations are performed, which increases a period of time during which the accuracy in detecting the oxygen concentration of exhaust gas is low.

SUMMARY OF THE INVENTION

It is therefore an object of the present invention to provide an oxygen sensor control apparatus configured such that, when an output value of an oxygen sensor greatly deviates from a predetermined range, a correction coefficient can be computed at an earlier timing, as compared with the case where the oxygen sensor deteriorates over time.

The above object of the invention has been achieved by providing (1) an oxygen sensor control apparatus which includes first storage means for storing a correction coefficient used for calibrating a relation between an output value of an oxygen sensor mounted to an exhaust pipe of an internal combustion engine and oxygen concentration of exhaust gas flowing through the exhaust pipe and which detects the oxygen concentration of the exhaust gas using the correction coefficient stored in the first storage means and the output value of the oxygen sensor. The oxygen sensor control apparatus comprises output value obtaining means for obtaining the output value of the oxygen sensor; representative value determination means for determining a representative value from at least one output value obtained by the output value obtaining means in a fuel cut period during which supply of fuel to the internal combustion engine is stopped, the representative value representing output values in the fuel cut period; first memorization control means for storing in second storage means the representative value in the fuel cut period determined by the representative value determination means; first range judgment means for judging whether or not a latest representative value, which is the latest representative value stored in the second storage means by the first memorization control means, falls outside a predetermined first range; second range judgment means for judging whether or not the latest representative value falls outside a predetermined second range, which contains the first range and is wider than the first range; first representative value judging means for judging whether or not a first judgment count has reached a first number of times equal to or greater than two times, the first judgment count representing a number of times the latest representative value is continuously judged by the first range judgment means to fall outside the first range and the latest representative value is continuously judged by the second range judgment means not to fall outside the second range; first computation means for computing a new value of the correction coefficient when the first representative value judging means judges that the first judgment count has reached the first number of times; second representative value judging means for judging whether or not a second judgment count has reached a second number of times smaller than the first number of times, the second judgment count representing a number of times the latest representative value is continuously judged by the second range judgment means to fall outside the second range; second computation means for computing a new value of the correction coefficient when the second representative value judging means judges that the second judgment count has reached the second number of times; and second memorization control means for storing in the first storage means the new value of the correction coefficient computed by the first computation means or the second computation means.

In the case where the oxygen sensor deteriorates with time, due to gradual deterioration of the oxygen sensor, the representative value, which represents the output values in a fuel cut period, changes from a value falling within the first range to a value falling outside the first range and falling within the second range. When the number of times the representative value is continuously judged to fall outside the first range and fall within the second range reaches the first number of times, the correction coefficient is computed by the first computation means. Meanwhile, in the case where the oxygen sensor is exchanged, the representative value deviates from the first range, and the representative value may be continuously judged to fall outside the second range. When the number of times the representative value is continuously judged to fall outside the second range reaches the second number of times, the correction coefficient is computed by the second computation means. Since the second number of times is smaller than the first number of times, when the representative value falls outside the second range, the correction coefficient can be computed at an earlier timing, as compared with the case where the oxygen sensor deteriorates with time. As a result, in the case where the oxygen sensor is replaced with a new oxygen sensor and the new oxygen sensor is then used, the relation between the output value and the oxygen concentration of exhaust gas can be calibrated within a short time, whereby the oxygen concentration of exhaust gas can be detected accurately.

In a preferred embodiment (2) of the oxygen sensor control apparatus according to (1) above, the first number of times is three times or more; and the second number of times is two times or more but smaller than the first number of times. For example, in the case where the output value of the oxygen sensor fluctuates because it pulsates as a result of operation of the internal combustion engine or noise is superimposed on the output thereof, the representative value may fall outside the second range. However, the second number of times is two times or more. Therefore, even in the case where the second number of times is two, the correction coefficient is not computed unless both the latest representative value and the representative value immediately before the latest representative value fall outside the second range. Since the correction coefficient is not computed unless the continuous representative values, the number of which is equal to the second number of times, fall outside the second range, it is possible to reduce instances of erroneous computation of the correction coefficient, which erroneous computation may occur due to detection of noise or pulsation caused by operation of the internal combustion engine.

In another preferred embodiment (3) of the oxygen sensor control apparatus according to (1) or (2) above, the oxygen sensor control apparatus may be configured such that the first computation means, which operates when the first representative value judging means judges that the first judgment count has reached the first number of times, computes a new value of the correction coefficient on the basis of the representative value stored in the second storage means and a preset reference value such that a corrected value obtained by multiplying the output value in the fuel cut period by the correction coefficient approaches the reference value; and the second computation means, which operates when the second representative value judging means judges that the second judgment count has reached the second number of times, computes a new value of the correction coefficient on the basis of the representative value stored in the second storage means and the reference value such that the corrected value approaches the reference value. In this case, the first computation means and the second computation means can accurately compute a new correction coefficient on the basis of the representative value and the reference value such that the corrected value approaches the preset reference value. Therefore, the relation between the output value of the oxygen sensor and the oxygen concentration of exhaust gas can be accurately calibrated through use of the computed correction coefficient.

In yet another preferred embodiment (4) of the oxygen sensor control apparatus according to (3) above, the oxygen sensor control apparatus may be configured such that the reference value falls within the first range and falls within the second range; the representative value determination means determines a value which represents corrected values in the fuel cut period, as the representative value, on the basis of at least one of the corrected values each obtained by multiplying, by the correction coefficient, the output value obtained by the output value obtaining means in the fuel cut period; the first computation means, which operates when the first representative value judging means judges that the first judgment count has reached the first number of times, computes a new value of the correction coefficient by dividing the reference value by a value obtained by dividing the representative value by a current value of the correction coefficient stored in the first storage means; and the second computation means, which operates when the second representative value judging means judges that the second judgment count has reached the second number of times, computes the new value of the correction coefficient by dividing the reference value by the value obtained by dividing the representative value by the current value of the correction coefficient stored in the first storage means. In this case, each of the first computation means and the second computation means computes a new correction coefficient by dividing the reference value by a value obtained by dividing the representative value by the current correction coefficient. Therefore, the relation between the output value of the oxygen sensor and the oxygen concentration of exhaust gas can be accurately calibrated through use of the computed correction coefficient.

In yet another preferred embodiment (5) of the oxygen sensor control apparatus according to (3) or (4) above, the oxygen sensor control apparatus may be configured such that the first computation means, which operates when the first representative value judging means judges that the first judgment count has reached the first number of times, computes the correction coefficient on the basis of the reference value and a first average value, which is the average of at least two of representative values which fall outside the first range and fall within the second range; and the second computation means, which operates when the second representative value judging means judges that the second judgment count has reached the second number of times, computes the correction coefficient on the basis of the reference value and a second average value, which is the average of at least two of representative values which fall outside the second range. The representative value determined by the representative value determination means may vary due to, for example, variation of operating conditions immediately before the start of fuel cut. The influence of the variation of the representative value can be reduced by computing the correction coefficient by use of the average of the representative values. Therefore, a stable correction coefficient can be computed.

DESCRIPTION OF REFERENCE NUMERALS

Reference numerals used to identify various features in the drawings include the following
1: engine control system
2: CPU
4: RAM
8: nonvolatile memory
10: oxygen sensor control apparatus
20: mounted oxygen sensor
81: first range
82: second range
100: internal combustion engine
120: exhaust pipe
Ipa: reference value
Ipb: output value
Ipc: corrected value
Ipd, Ipf, Ipg: weighted average
Ipe: representative value
Kp: correction coefficient

DETAILED DESCRIPTION OF THE PREFERRED EMBODIMENTS

An embodiment of the present invention will now be described with reference to the drawings. Notably, the drawings are used for describing the technical features which can be employed by the present invention. The configuration of an apparatus, the flowcharts of various processing, etc., shown in the drawings are mere examples, and the invention should not be construed as being limited thereto.

Figure 1:
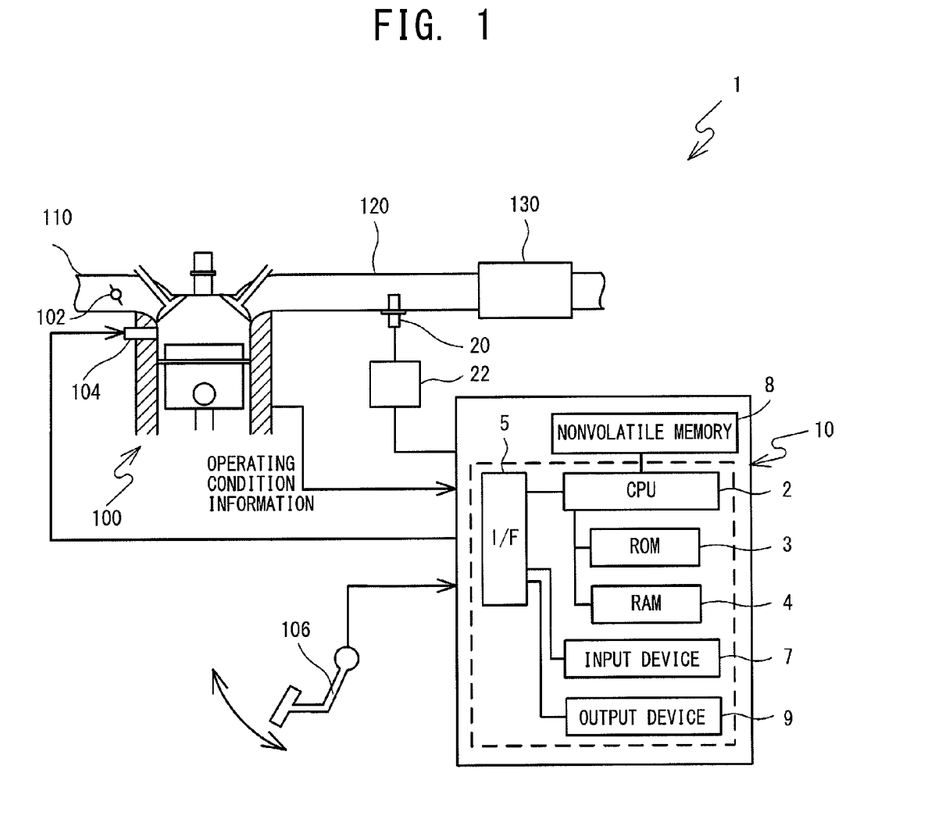
FIG. 1 is a schematic diagram showing the physical and electrical configurations of an engine control system 1 including an oxygen sensor control apparatus 10.

FIG. 1 is a schematic diagram of an engine control system 1 including an oxygen sensor control apparatus 10. In the engine control system 1, an oxygen sensor 20 is mounted to an exhaust pipe 120 of an internal combustion engine 100 of a vehicle (hereinafter, the oxygen sensor 20 will also be referred to as the "mounted oxygen sensor 20"), and a controller 22 is connected to the mounted oxygen sensor 20. The oxygen sensor control apparatus 10 is connected to the controller 22. The oxygen sensor control apparatus 10 according to the present embodiment functions as an engine control unit (ECU).

A throttle valve 102 is provided in an intake pipe 110 of the internal combustion engine 100, and an injector 104 is disposed on each cylinder of the internal combustion engine 100 so as to supply fuel into the cylinder. An exhaust gas purification catalyst 130 is attached to a downstream portion of the exhaust pipe 120. Various, unillustrated sensors (a pressure sensor, a temperature sensor, a crank angle sensor, etc.) are attached to the internal combustion engine 100, and an unillustrated air-flow meter is disposed in the intake pipe 110. Operating condition information (the pressure, temperature, and rotational speed of the engine, the supply quantity of air, etc.) from the various sensors and the air-flow meter is fed to the oxygen sensor control apparatus 10. The oxygen sensor control apparatus 10 controls the throttle valve 102 to thereby control the quantity of air supplied to the internal combustion engine 100 and controls the quantity of fuel injected from the injector 104, in accordance with the above-mentioned operating condition information, the oxygen concentration of exhaust gas detected by the mounted oxygen sensor 20, the amount by which an accelerator pedal 106 is depressed by a driver, etc. Thus, the oxygen sensor control apparatus 10 operates the internal combustion engine 100 at a proper air-fuel ratio.

The oxygen sensor control apparatus 10 is a unit in which a microcomputer and a nonvolatile memory 8 such as an EEPROM are mounted on a circuit board. The microcomputer includes a central processing unit (CPU) 2, ROM 3, RAM 4, an interface circuit (I/F) 5 for external devices, an input device 7 for inputting data from the outside, and an output device 9 for outputting data to the outside. The oxygen sensor control apparatus 10 (CPU 2) processes an input signal in accordance with a program stored in the ROM 3 in advance and outputs from the output device 9 a control signal for controlling the quantity of fuel injected by the injector 104. The oxygen sensor control apparatus 10 also performs main processing which will be described below.

The mounted oxygen sensor 20 is a so-called two-cell-type air-fuel-ratio sensor which includes two cells each composed of an oxygen-ion conductive solid electrolyte and a pair of electrodes provided thereon. Specifically, the mounted oxygen sensor 20 has a housing which holds a gas detection element therein and which is attached to the exhaust pipe 120. The gas detection element includes an oxygen pump cell and an oxygen concentration detection cell, which are stacked together with a hollow measurement chamber formed therebetween. Exhaust gas is introduced into the measurement chamber via a porous member. Further, a heater is stacked on the two cells so as to heat these cells to an activation temperature. Notably, in order to distinguish the oxygen sensor 20 actually mounted onto an individual internal combustion engine from a reference oxygen sensor described below, in the present embodiment, the oxygen sensor 20 mounted onto the engine will be referred to as the "mounted oxygen sensor."

The mounted oxygen sensor 20 is connected to the controller 22, which is a well known detection circuit including various resistors, differential amplifiers, etc. The controller 22 supplies pump current to the mounted oxygen sensor 20, converts the pump current to voltage, and outputs the voltage to the oxygen sensor control apparatus 10 as an oxygen concentration detection signal. More specifically, the controller 22 controls the supply of electric current to the oxygen pump cell such that the output of the oxygen concentration detection cell becomes constant. In this case, the oxygen pump cell pumps oxygen within the measurement chamber to the outside, or pumps oxygen into the measurement chamber. At that time, a pump current flows through the oxygen pump cell. The controller 22 coverts this pump current to voltage via a detection resistor, and outputs the voltage to the oxygen sensor control apparatus 10. Notably, the pump current and the voltage output from the controller 22 are equivalent to each other because they both correspond to the oxygen concentration within the exhaust pipe 120. In view of this, the oxygen sensor control apparatus 10 indirectly detects the pump current by detecting the voltage output from the controller 22. Therefore, in the following description, the value of the pump current detected by the oxygen sensor control apparatus 10 (CPU 2) will be referred to as the "output value Ipb" of the mounted oxygen sensor 20. A change in the output value Ipb corresponds to a change in the oxygen concentration within the exhaust pipe 120.

Next, a correction coefficient Kp will be described. The correction coefficient Kp is a coefficient used for calibrating the relation between oxygen concentration and the output value Ipb of the mounted oxygen sensor 20 attached to the internal combustion engine 100, and is stored in the nonvolatile memory 8. In the following description, an ideal oxygen sensor; i.e., a standard oxygen sensor which has the same structure as that of the mounted oxygen sensor 20 and an output characteristic at the center of a range of manufacturing variation thereof, will be referred to as a "reference oxygen sensor." Also, the value of current output from the reference oxygen sensor when it is exposed to the ambient atmosphere (oxygen concentration: about 20.5%) will be referred to as a "reference value Ipa." In the present embodiment, the reference value Ipa is "4 mA."

The correction coefficient Kp is determined such that a value (hereinafter referred to as a "corrected value Ipc") obtained by multiplying the output value Ipb of the mounted oxygen sensor 20 by the correction coefficient Kp approaches the output value Ipb of the reference oxygen sensor. For example, in the case where the corrected value Ipc obtained when the mounted oxygen sensor 20 is exposed to the ambient atmosphere becomes equal to the reference value Ipa (4 mA), the corrected value Ipc obtained from the output value Ipb of the mounted oxygen sensor 20 becomes equal to the output value of the reference oxygen sensor. As described above, by using the corrected value Ipc, the influence of the characteristic variation (attributable to individual difference) and deterioration of the mounted oxygen sensor 20 can be mitigated, whereby oxygen concentration can be detected with an accuracy comparable to that in the case where a reference oxygen sensor is used. Therefore, the quantity of fuel injected from the injector 104 can be controlled to a proper quantity. Notably, the correction coefficient Kp is stored in the nonvolatile memory 8. Furthermore, in the present embodiment, the correction coefficient Kp is computed (updated) on the basis of the output value Ipb of the mounted oxygen sensor 20 in a period during which the supply of fuel to the internal combustion engine 100 is stopped (fuel cut). Since no fuel is injected from the injector 104 during the fuel cut period, the atmosphere within the exhaust pipe 120 approaches the ambient atmosphere, and, through comparison with the reference value Ipa (the output value of the reference oxygen sensor when exposed to the ambient atmosphere), the correction coefficient Kp can be computed. The computation of the correction coefficient Kp will be described in detail below.

Figure 2:
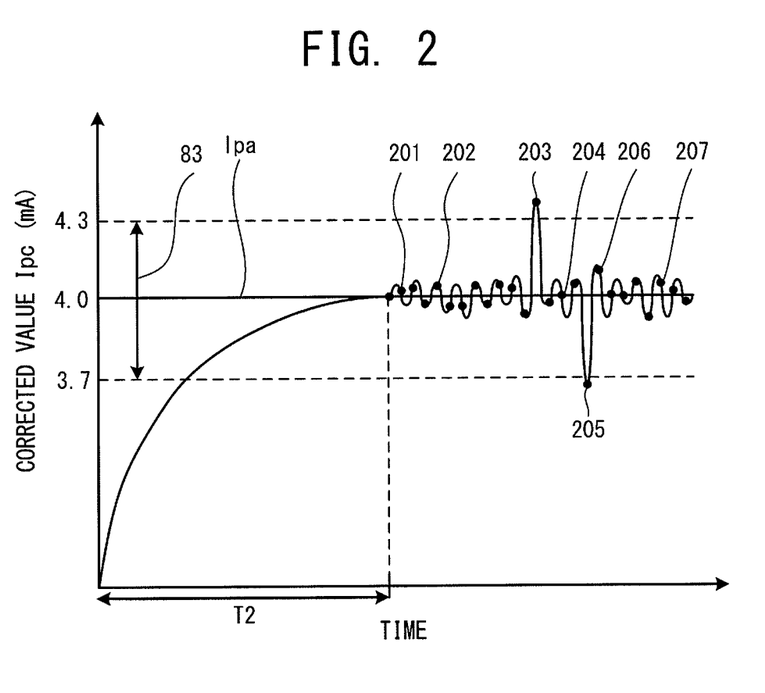
FIG. 2 is a graph showing an example change in a corrected value Ipc based on an output value Ipb of a mounted oxygen sensor 20 in a fuel cut period.

Next, an example change in the corrected value Ipc obtained from the output value Ipb of the mounted oxygen sensor 20 during a single fuel cut period will be described with reference to FIG. 2. FIG. 2 shows the relation between the time after the start of fuel cut and the corrected value Ipc based on the output value of the mounted oxygen sensor 20. Even when fuel cut is started, exhaust gas produced before the start of fuel cut remains within the exhaust pipe 120, etc., and a time is needed for replacement of the exhaust gas with ambient air. Thus, a time is needed for the oxygen concentration within the exhaust pipe 120 to become equal to the oxygen concentration of the ambient air. Therefore, the corrected value Ipc increases gradually (the period of time T2 in FIG. 2). When the oxygen concentration within the exhaust pipe 120 approaches the oxygen concentration of the ambient air, the corrected value Ipc becomes nearly stable. However, even after the oxygen concentration within the exhaust pipe 120 has approached the oxygen concentration of the ambient air, the corrected value Ipc fluctuates (pulsates) due to the influence of the operating conditions of the internal combustion engine 100 and superimposition of noise. Notably, during the period of time T2 in FIG. 2, the corrected value Ipc increases gradually while pulsating. However, such pulsation is not shown in FIG. 2.

Next, the main processing performed by the CPU 2 of the oxygen sensor control apparatus 10 will be described with reference to FIGS. 3 and 4. The main processing is started upon supply of electric power to the oxygen sensor control apparatus 10. As a result of execution of the main processing, the timing of computation of a new correction coefficient Kp performed when the mounted oxygen sensor 20 is exchanged becomes earlier than the timing of computation of a new correction coefficient Kp performed when the mounted oxygen sensor 20 deteriorates with time. In the following description, a variable M represents the number of times a certain condition (which will be described in detail below) is satisfied continuously, and a variable P represents the number of times another condition (which will be described in detail below) is satisfied continuously. A variable N represents the number of times the weighted average Ipd is computed during each fuel cut period. The weighted average Ipd represents the weighted average of corrected values Ipc obtained during each fuel cut period, and time T1 represents the time elapsed after the start of the fuel cut period. Each step in the flowcharts will be abbreviated to "S."

Figure 3:
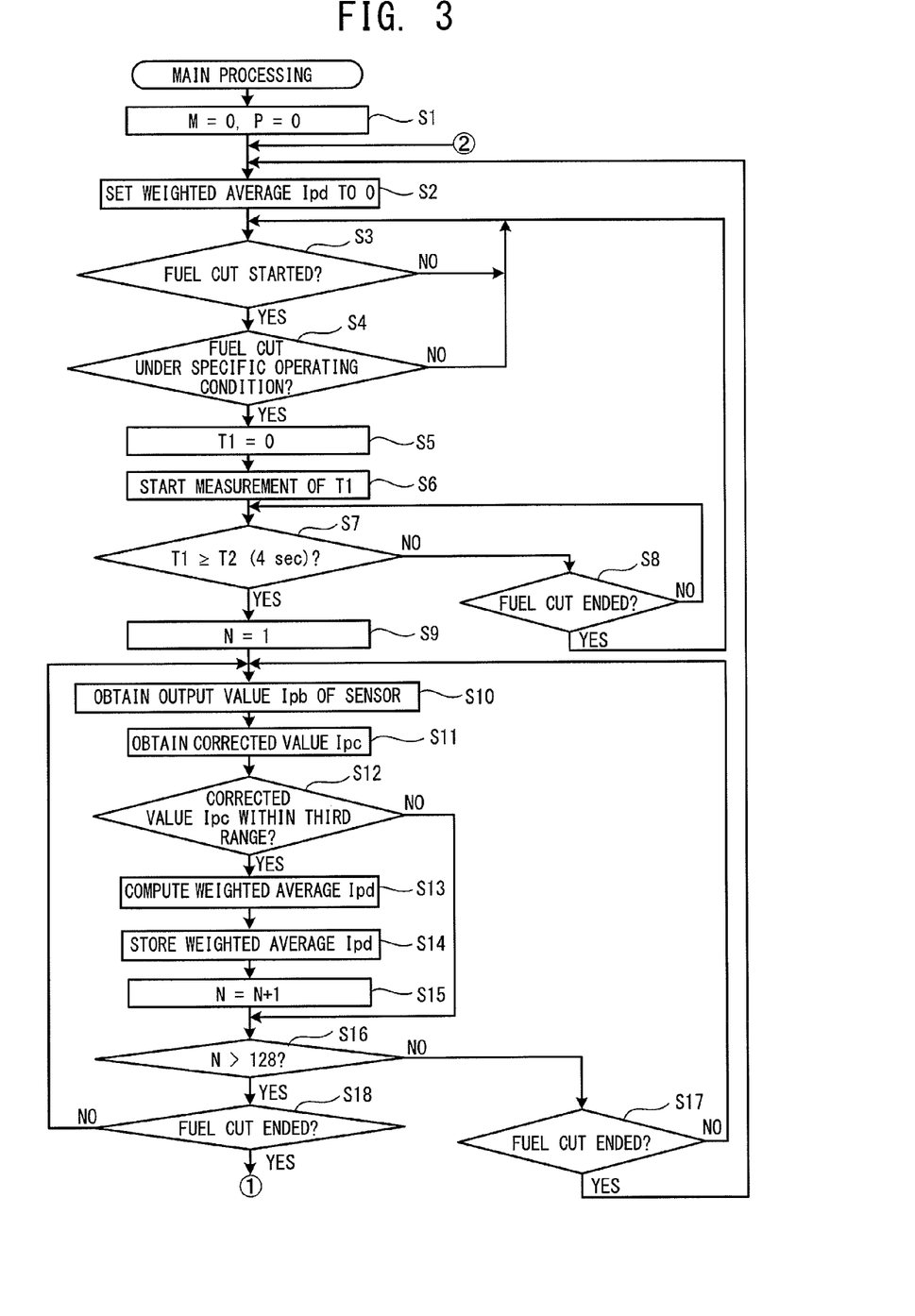
FIG. 3 is a flowchart showing main processing.

As shown in FIG. 3, in the main processing, the CPU 2 sets the variable M and the variable P to "0" (S1). Notably, the values of the variable M and the variable P are stored in the RAM 4 (the weighted average Ipd, the variable N, the time T1, which will be described below, are also stored in the RAM 4). Next, the CPU 2 sets the weighted average Ipd to "0" (S2). Subsequently, the CPU 2 judges whether or not fuel cut has been newly started during operation of the internal combustion engine 100 (S3). Notably, in the internal combustion engine 100, the oxygen sensor control apparatus 10 outputs an instruction for reducing the quantity of fuel injected from the injector 104 to zero, in accordance with operating conditions such as deceleration of the vehicle or the quantity of intake air. In S3, the CPU 2 judges whether or not the fuel cut has been started, by judging whether or that instruction has been output. When the fuel cut has not yet been started (S3: NO), the CPU 2 returns to S3.

In the case where fuel cut has been started (S3: YES), the CPU 2 judges whether or not fuel cut has been started under a certain operating condition (S4). Notably, for judging whether or not fuel cut has been started under the certain operating condition during operation of the internal combustion engine 100, the CPU 2 uses at least one of parameters representing the operating conditions (engine speed, engine load, intake air quantity) of the internal combustion engine 100 immediately before the start of the fuel cut. When the parameter(s) satisfies a predetermined condition (that is, a previously set condition suitable for computation of the correction coefficient Kp), the CPU 2 judges that fuel cut has been started under the certain operating condition.

In the case where fuel cut has not yet been started under the certain operating condition (S4: NO), the CPU 2 returns to S3.

In the case where fuel cut has been started under the certain operating condition (S4: YES), the CPU 2 sets the time T1 to "0" (S5). Subsequently, the CPU 2 starts measurement of the time T1 (S6). Next, the CPU 2 judges whether or not the time T1 is equal to or longer than a time T2 (e.g., 4 sec) (S7). In the case where the time T1 is not equal to or longer than the time T2 (S7: NO), the CPU 2 judges whether or not the fuel cut has been ended (S8). In the case where the fuel cut has not yet been ended (S8: NO), the CPU 2 returns to S7. That is, the oxygen sensor control apparatus 10 waits until the time T1 elapsed after the start of the fuel cut becomes equal to or longer than the time T2, or until the fuel cut ends before that.

As shown in FIG. 2, the time T2 is set to a time during which the oxygen concentration within the exhaust pipe 120 approaches the oxygen concentration of the ambient air and the corrected value Ipc becomes generally stable. Therefore, by judging in S7 whether or not the time T1 has become equal to or longer than the time T2, the CPU 2 judges whether or not the oxygen concentration within the exhaust pipe 120 has approached the oxygen concentration of the ambient air.

In the case where the fuel cut ends before the time T1 becomes equal to or longer than the time T2 (S8: YES), the CPU 2 returns to S3. In the case where the fuel cut has continued and the time T1 has become equal to or longer than the time T2 (S7: YES), the CPU 2 sets the variable N to "1" (S9). Subsequently, the CPU 2 obtains the output value Ipb of the mounted oxygen sensor 20 (S10). Notably, S10 is repeatedly executed during the fuel cut period. In the present embodiment, S10 is repeatedly executed at intervals of 1 ms. Subsequently, the CPU 2 multiplies the output value Ipb obtained in S10 by the correction coefficient Kp stored in the nonvolatile memory 8, to thereby obtain (compute) the corrected value Ipc (S11). In FIG. 2, the corrected value Ipc computed on the basis of the output value Ipb obtained in S10 is shown by a circular black dot. Notably, in the following description, when a specific corrected value is described, it is denoted by a reference numeral (e.g., a corrected value 201, etc.); and, when a plurality of corrected values are described without distinguishing them from one another, they will be described as the corrected value(s) Ipc (the same rule applies to a representative value Ipe, which will be described below).

Next, the CPU 2 judges whether or not the corrected value Ipc computed in S11 falls within a third range 83 (see FIG. 2) (S12). The third range 83 is used to prevent the corrected value Ipc from being used for computing a weighted average Ipd to be described below, if the corrected value Ipc greatly deviates from the reference value Ipa due to influences of the operating conditions of the internal combustion engine 100, noise, etc. In the present embodiment, the third range 83 is "the reference value Ipa (4 mA)±7.5%"; that is, 3.7 mA to 4.3 mA. Notably, the expression "the corrected value Ipc falls within the third range 83" encompasses the case where the corrected value Ipc is 3.7 mA or 4.3 mA, which are thresholds; and an expression "the corrected value Ipc falls outside the third range 83" means that the corrected value Ipc is neither 3.7 mA nor 4.3 mA, which are thresholds, and is not contained within the third range 83 (this rule also applies to a first range 81 and a second range 82, which will be described below).

In the case where the corrected value Ipc falls within the third range 83 (see, for example, corrected values 201, 202, 204, 206, and 207 shown in FIG. 2) (S12: YES), the CPU 2 proceeds to S13, which will be described below. Meanwhile, in the case where the corrected value Ipc falls outside the third range 83 (see, for example, corrected values 203 and 205 shown in FIG. 2) due to the influence of the operating conditions of the internal combustion engine 100, noise, etc. (S12: NO), the CPU 2 proceeds to S16, which will be described below. That is, the weighted average Ipd is not computed in S13 (to be described below), and the corrected value Ipc computed in S11 is not used. Since corrected values Ipc which greatly deviate from the reference value Ipa due to the influence of the operating conditions of the internal combustion engine 100, noise, etc., are not used for computing the weighted average Ipd, the correction coefficient Kp can be computed more accurately in S27 and S30, which will be described below.

In the case where the corrected value Ipc falls within the third range 83 (S12: YES), the corrected value Ipc is used for computing the weighted average Ipd. Notably, in S13, the CPU 2 computes the weighted average Ipd by using 128 or more corrected values Ipc during a single fuel cut period. Since 128 or more corrected values Ipc are used, the influence of pulsation of the output value, noise, etc. during the fuel cut period can be reduced. The weighted average Ipd is computed in accordance with the following equation (1).

$$Ipd = 1/128 \times \{\text{latest } Ipc - Ipd(N-1)\} + Ipd(N-1) \quad (1)$$

"Ipd(N−1)" of the equation (1) corresponds to the weighted average Ipd computed in S13 in the previous program execution cycle. Notably, since "Ipd(N−1)" does not exist when the variable N=1, the CPU 2 computes the weighted average Ipd by using, as "Ipd(N−1)," the corrected value Ipc obtained when N=1 (that is, the corrected value Ipc obtained first after the start of the fuel cut).

After the execution of S13, the CPU 2 stores in the RAM 4 the weighted average Ipd computed in S13 (S14). Subsequently, the CPU 2 increases the variable N by an increment of 1 (S15). Next, the CPU 2 judges whether or not the variable N is greater than "128" (S16). In the case where the variable N is not greater than "128" (S16: NO), the CPU 2 judges whether or not the fuel cut has been ended (S17). In the case where the fuel cut has been ended before the variable N has reached "128" (S17: YES), the CPU 2 returns to S2 and sets the weighted average Ipd to "0." That is, S19 to S31, which will be described below, are not executed, and the weighted average Ipd is not used. In the case where the fuel cut has not yet been ended (S17: NO), the CPU 2 returns to S10.

When the variable N becomes greater than "128" (S16: YES), the CPU 2 judges whether not the fuel cut has been ended (S18). In the case where the CPU 2 judges that the fuel cut has been ended (S18: YES), the CPU 2 proceeds to S19 and chooses (determines), as a representative value Ipe, the weighted average Ipd finally stored in S14 (in other words, the latest weighted average Ipd) (S19). The representative value Ipe is a value which represents the output values during a single fuel cut period. In the present invention, the representative value Ipe is the weighted average Ipd of the corrected values Ipc each computed on the basis of the output value. Next, the CPU 2 stores in the RAM 4 the representative value Ipe determined in S19 (S20). That is, for each fuel cut period, one representative value Ipe is determined (S19) and stored (S20). Meanwhile, in the case where the CPU 2 judges in S18 that the fuel cut has not yet been ended (S18: NO), the CPU 2 returns to S10.

After execution of S20, the CPU 2 judges whether or not the latest representative value Ipe stored in the RAM 4 falls outside the second range 82 (S21). As shown in FIG. 5, in the present embodiment, the second range 82 is "the reference value Ipa (4 mA)±2%"; that is, from 3.92 mA to 4.08 mA.

Here, FIG. 5 will be described. FIG. 5 shows the relation between the number of fuel cut operations and the representative value Ipe. Representative values 301 to 317 are example values of the representative value Ipe determined in S19 for each fuel cut period and stored in the RAM 4 in S20. Representative values 301 to 304 and representative values 315 to 317 fall within the first range 81 (which will be described below). Ten representative values 305 to 314 fall outside the first range 81 and fall within the second range 82.

Figure 4:
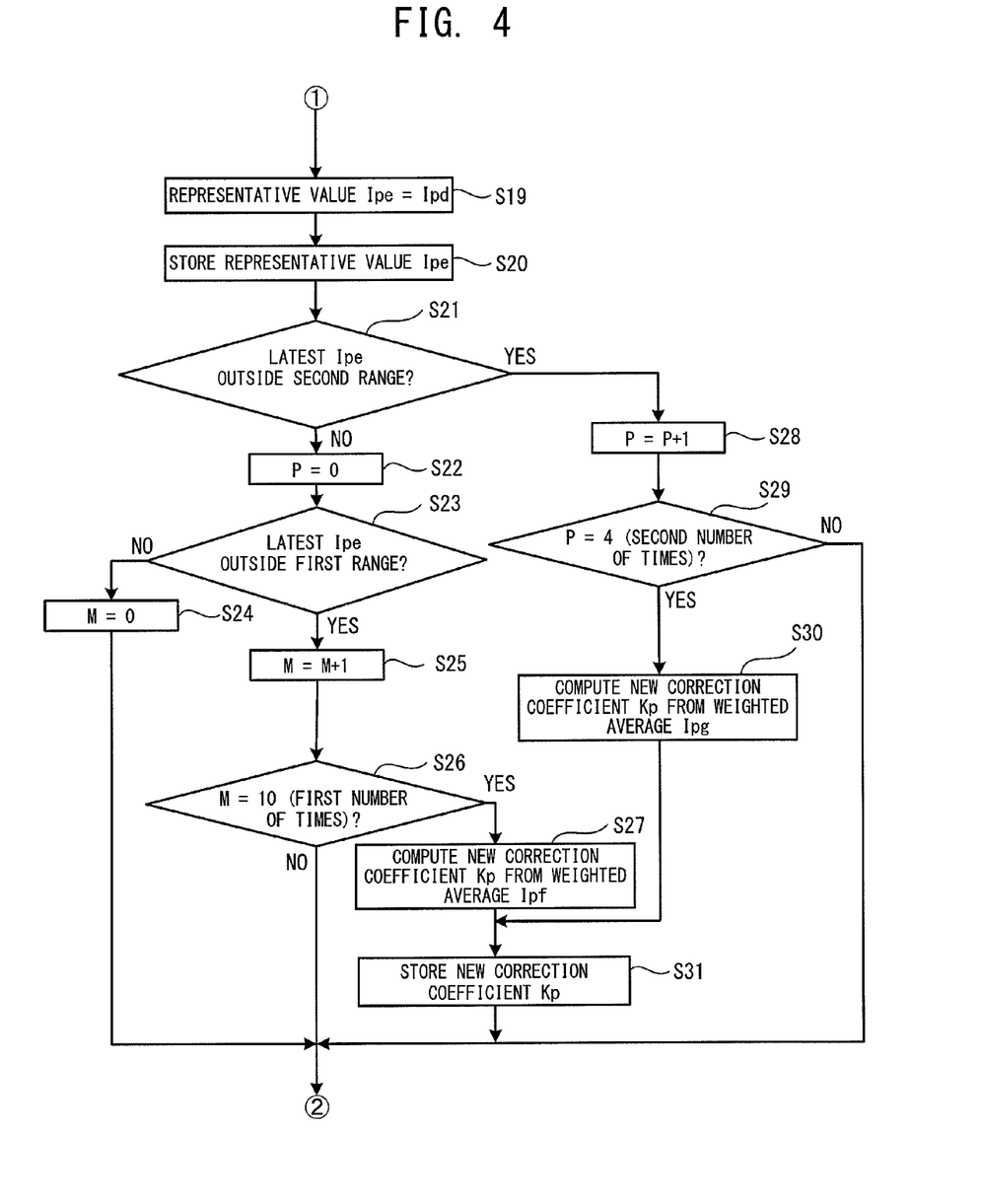
FIG. 4 is a flowchart showing the main processing.
Figure 5:
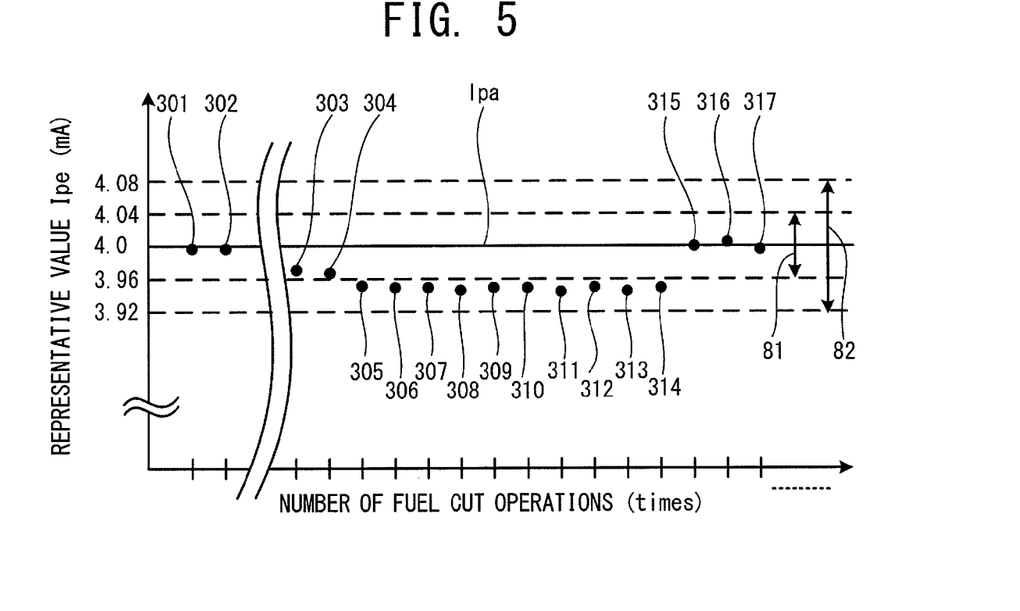
FIG. 5 is a graph showing an example change in a representative value Ipe for each fuel cut.

Referring back to the flowchart of FIG. 4, in the case where the latest representative value Ipe is the representative value 301 (see FIG. 5), the CPU 2 judges that the latest representative value Ipe does not fall outside the second range 82 (S21: NO), and sets the variable P to "0" (S22).

Next, the CPU 2 judges whether or not the latest representative value Ipe stored in the RAM 4 falls outside the first range 81 (S23). The first range 81 is set to fall within the second range 82. That is, the first range 81 is contained in the second range 82. In the present embodiment, the first range 81 is "the reference value Ipa (4 mA)±1%"; that is, 3.96 mA to 4.04 mA. For example, in the case where the latest representative value Ipe is the representative value 301 (see FIG. 5), the CPU 2 judges that the latest representative value Ipe does not fall outside the first range 81 (S23: NO), and sets the variable M to "0" (S24). Subsequently, the CPU 2 returns to S2. When the next fuel cut is started, the CPU 2 continues the processing for obtaining the representative value Ipe, etc.

For example, in the case where the latest representative value Ipe is the representative value 305 (see FIG. 5), the variable M is increased by an increment of 1 (S25) because the representative value 305 does not fall outside the second range 82 (S21: NO) and falls outside the first range 81 (S23: YES). Next, the CPU 2 judges whether or not the variable M is "10" (S26). This "10" will be referred to as the first number of times. In the case where the situation in which the latest representative value Ipe is judged not to fall outside the second range 82 (S21: NO) and is judged to fall outside the first range 81 (S23: YES) continuously occurs 10 times, the variable M becomes "10" in S25. Meanwhile, in the case where the latest representative value Ipe is judged not to fall outside the first range 81 before the variable becomes "10" (S23: NO), the variable M becomes "0" (S24). That is, in S26, the CPU 2 judges whether or not the number of times the latest representative value Ipe is continuously judged not to fall outside the second range 82 (S21: NO) and is judged to fall outside the first range 81 (S23: YES) reaches 10 (the first number of times), by judging whether or not the variable M is "10." Notably, although in the present embodiment the first number of times is "10," the first number of times may be "30." The value of the variable M corresponds to the "first judgment count" of the present invention.

In the case where the variable M is not "10" (S26: NO), the CPU 2 returns to S2. The following description will be provided for an example case where the mounted oxygen sensor 20 deteriorates with time. In the case where the mounted oxygen sensor 20 deteriorates with time, the representative value Ipe gradually deviates from the reference value Ipa, and the representative value Ipe falls within the second range 82 and falls outside the first range 81 ten times continuously (see, for example, the representative value 305 to 314 shown in FIG. 5). In such a case, since the variable M becomes "10" (S25), the CPU 2 judges that the variable M is "10" (S26: YES). Subsequently, the CPU 2 computes a new correction coefficient Kp (S27). In S27, the CPU 2 computes a new correction coefficient Kp by the following procedure. First, the CPU 2 computes the weighted average Ipf of the ten representative values 305 to 314, which fall within the second range 82 and fall outside the first range 81, in accordance with the following equation (2).

$$Ipf=1/10\{Ipe-Ipf(L-1)\}+Ipf(L-1) \quad (2)$$

"Ipf(L−1)" of the equation (2) is the weighted average computed most recently. When the weighted average Ipf is computed, ten representative values Ipe (from the oldest representative value 305 to the latest representative value 314) are successively substituted for "Ipe" of equation (2), whereby the weighted average Ipf is updated. Notably, since "Ipf(L−1)" does not exist immediately after the start of computation of the weighted average Ipf, the weighted average Ipf is computed by substituting the first (oldest) representative value 305 for "Ipf(L−1)."

After computing the weighted average Ipf of the ten representative values Ipe, the computed weighted average Ipf is divided by the current correction coefficient Kp. Further, the reference value Ipa is divided by the computed value, whereby a new correction coefficient Kp is computed (that is, the new correction coefficient Kp=the reference value Ipa/(the weighted average Ipf/the current correction coefficient Kp)). For example, in the case where the current correction coefficient is "1.05" and the weighted average Ipf is "3.95 mA," "3.95" is divided by "1.05," whereby "3.762" is obtained as the computed value. The reference value Ipa (4 mA) is divided by "3.762," whereby "1.063" is obtained as the new correction coefficient Kp (S27).

After computing the new correction coefficient Kp in S27, the CPU 2 stores the computed correction coefficient Kp in the nonvolatile memory 8 for update (S31). That is, the CPU 2 calibrates the relation between oxygen concentration and the output value of the mounted oxygen sensor 20 attached to the internal combustion engine 100. After that, the CPU 2 returns to S2.

In the processing afterwards, since the corrected value Ipc is computed using the updated correction coefficient Kp (S11), the representative value Ipe determined in S19 assumes a value close to the reference value Ipa (see, for example, the representative values 315 to 317 shown in FIG. 5). This is because the correction coefficient Kp is computed accurately in S27. Since the correction coefficient Kp is computed accurately, the CPU 2 can detect the oxygen concentration of exhaust gas accurately. Therefore, the internal combustion engine 100 can be operated at a proper air-fuel ratio.

Figure 6:
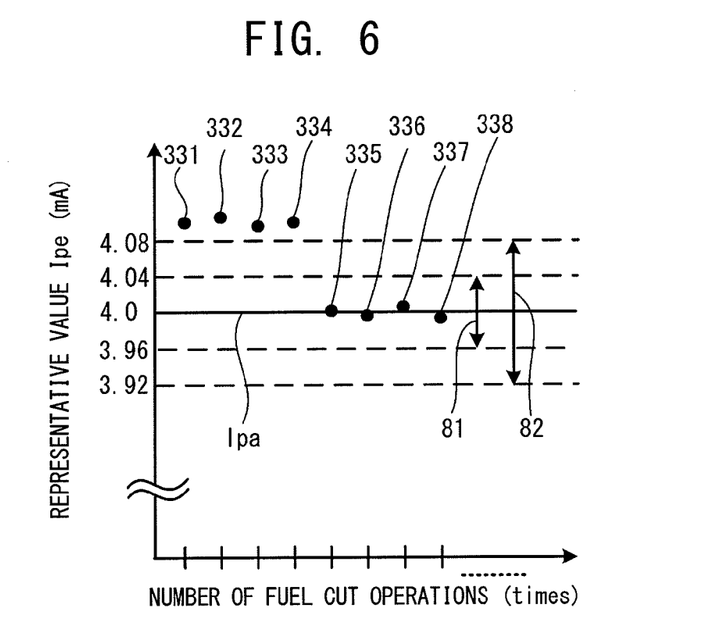
FIG. 6 is a graph showing an example change in a representative value Ipe for each fuel cut.

The following description will be provided for an example case where the mounted oxygen sensor 20 has been exchanged. In the case where the mounted oxygen sensor 20 has been exchanged, due to the difference (variation stemming from an individual difference) in characteristics and/or the difference in degree of deterioration between the previously mounted oxygen sensor 20 and the newly mounted oxygen sensor 20, in some cases, the representative value Ipe computed from the output value Ipb of the mounted oxygen sensor 20 greatly deviates from the first range 81 and falls outside the second range 82 (see, for example, representative values 331 to 334 shown in FIG. 6). Notably, like FIG. 5, FIG. 6 shows the relation between the number of fuel cut operations and the representative value Ipe.

For example, in the case where the latest representative value Ipe is the representative value 331, the CPU 2 judges that the representative value 331 falls outside the second range 82 (S21: YES), and increases the variable P by an increment of 1 (S28). Next, the CPU 2 judges whether or not the variable P is "4" (S29). This "4" will be referred to as the second number of times. The second number of times is smaller than the first number of times.

In the case where the latest representative value Ipe is continuously judged four times to fall outside the second range 82, the variable P becomes "4" in S28. Meanwhile, in the case where the latest representative value Ipe is judged not to fall outside the second range 82 before the variable P becomes "4" (S21: NO), the variable P becomes "0" (S22). That is, in S29, the CPU 2 judges whether or not the number of times the representative value Ipe is continuously judged to fall outside the second range 82 (S21: YES) reaches 4 (the second number of times), by judging whether or not the variable P is "4." Notably, although the second number of times is 4 times in the present embodiment, the second number of times may be two times or more but smaller than the first number of times. For example, the second number of times may be two times or eight times. The value of the variable P corresponds to the "second judgment count" of the present invention.

In the case where the variable P is not "4" (S29: NO), the CPU 2 returns to S2. For example, in the case where the representative value Ipe is continuously judged four times to fall outside the second range 82 (see, for example, the representative values 331 to 334 shown in FIG. 6), the variable P becomes "4" (S28). Therefore, the CPU 2 judges that the variable P is "4" (S29: YES). Subsequently, the CPU 2 computes a new correction coefficient Kp (S30). In S27, the CPU 2 computes the new correction coefficient Kp on the basis of the representative value Ipe and the reference value Ipa such that the corrected value Ipc, which is obtained by multiplying the output value Ipb during the fuel cut period by the correction coefficient Kp, approaches the reference value Ipa set in advance. Specifically, the CPU 2 computes the weighted average Ipg of the four representative values 331 to 334, which fall outside the second range 82, in accordance with the following equation (3).

$$Ipg=1/4\{Ipe-Ipg(Q-1)\}+Ipg(Q-1) \quad (3)$$

"Ipg(Q−1)" of the equation (3) is the weighted average computed most recently. When the weighted average Ipf is computed, the four representative values Ipe (from the oldest representative value 331 to the latest representative value 334) are successively substituted for "Ipe" of the equation (3), whereby the weighted average Ipg is updated. Notably, since "Ipg(Q−1)" does not exist immediately after the start of computation of the weighted average Ipg, the weighted average Ipg is computed by substituting the first (oldest) representative value 311 for "Ipg(Q−1)."

After computing the weighted average Ipg of the four representative values Ipe, as in the case of S27, the computed weighted average Ipg is divided by the current correction coefficient Kp, and the reference value Ipa is divided by the computed value, whereby the new correction coefficient Kp is computed (S30).

Next, the CPU 2 proceeds to S31, and updates the correction coefficient Kp stored in the nonvolatile memory 8 with the new correction coefficient Kp computed in S30. That is, the CPU 2 calibrates the relation between oxygen concentration and the output value Ipb of the mounted oxygen sensor 20 attached to the internal combustion engine 100. In the processing afterwards, since the corrected value Ipc is computed by use of the updated correction coefficient Kp (S11), the representative value Ipe determined in S19 assumes a value close to the reference value Ipa (see, for example, the representative values 335 to 338 shown in FIG. 6). This is because the correction coefficient is computed accurately in S30. Since the correction coefficient is computed accurately, the CPU 2 can detect the oxygen concentration of exhaust gas accurately. Therefore, the internal combustion engine 100 can be operated at a proper air-fuel ratio.

The main processing of the present embodiment is executed as described above. In the present embodiment, the first number of times (see S29) is smaller than the second number of times (see S26). Therefore, for example, in the case where the representative value Ipe falls outside the second range 82 as a result of exchange of the mounted oxygen sensor 20, a new correction coefficient Kp can be computed at an earlier timing (S30), as compared with the case where the mounted oxygen sensor 20 deteriorates with time. As a result, in the case where the oxygen sensor is replaced with a new oxygen sensor and the new oxygen sensor is then used, the relation between the output value Ipb of the mounted oxygen sensor 20 and the oxygen concentration of exhaust gas can be calibrated within a short time, whereby the oxygen concentration of exhaust gas can be detected accurately.

Also, in the case where the representative value Ipe is continuously judged ten times to fall within the second range 82 and to fall outside the first range 81 (S26: YES), the correction coefficient Kp is computed (S27). That is, a new correction coefficient Kp is not computed unless the state in which the representative value Ipe falls within the second range 82 and falls outside the first range 81 continuously occurs a plurality of times. Furthermore, in the case where the representative value Ipe is continuously judged four times to fall outside the second range 82 (S29: YES), the correction coefficient Kp is computed (S30). That is, a new correction coefficient Kp is not computed unless the state in which the representative value Ipe falls outside the second range 82 continuously occurs a plurality of times. Therefore, it is possible to reduce the possibility of erroneous computation of the correction coefficient Kp, which erroneous computation may occur due to detection of pulsation caused by operation of the internal combustion engine, noise, etc.

In some cases, the representative value Ipe determined in S19 may vary due to a variation in operating conditions immediately before fuel cut. In the present embodiment, when the CPU 2 computes a new correction coefficient Kp in S27 or S30, the CPU 2 uses the weighted average Ipf or the weighted average Ipg, each of which is the weighted average of a plurality of representative values Ipe. Therefore, the influence of variation among the plurality of representative values Ipe can be reduced. Therefore, a stable correction coefficient Kp can be computed.

In the above-described embodiment, the mounted oxygen sensor 20 corresponds to the "oxygen sensor" of the present invention; and the nonvolatile memory 8 corresponds to the "first storage means" of the present invention. The CPU 2 which performs the processing of S10 of FIG. 3 corresponds to the "output value obtaining means" of the present invention; and the CPU 2 which performs the processing of S19 of FIG. 4 corresponds to the "representative value determination means" of the present invention. The RAM 4 corresponds to the "second storage means" of the present invention; and the CPU 2 which performs the processing of S20 corresponds to the "first memorization control means" of the present invention. The CPU 2 which performs the processing of S23 corresponds to the "first range judgment means" of the present invention; and the CPU 2 which performs the processing of S21 corresponds to the "second range judgment means" of the present invention. The CPU 2 which performs the processing of S26 corresponds to the "first representative value judging means" of the present invention; and the CPU 2 which performs the processing of S27 corresponds to the "first computation means" of the present invention. The CPU 2 which performs the processing of S29 corresponds to the "second representative value judging means" of the present invention; and the CPU 2 which performs the processing of S30 corresponds to the "second computation means" of the present invention. The CPU 2 which performs the processing of S31 corresponds to the "second memorization control means" of the present invention; and the weighted average Ipf corresponds to the "first average" of the present invention. The weighted average Ipg corresponds to the "second average" of the present invention.

Notably, the present invention is not limited to the above-described embodiment, and may be modified in various ways. In the above-described embodiment, the weighted average Ipd is computed by use of 128 or more corrected values Ipc. However, the processing of computing the weighted average Ipd is not limited thereto. For example, the weighted average Ipd is computed by use of corrected values Ipc which are obtained (computed) until at least a predetermined period time (e.g., 1 sec) elapses after the time T1 has been judged to be equal to or greater than the time T2 (S7: YES) (in other words, for 5 sec after the start of fuel cut). In this case, the processing of the CPU 2 in S16 (see FIG. 3) may be modified as follows. The CPU 2 judges in S16 whether or not 5 sec has elapsed after the start of fuel cut (that is, whether or not the time T1 is 5 sec or longer). When 5 sec has not yet elapsed (S16: NO), the CPU 2 proceeds to S17. When 5 sec has elapsed (S16: YES), the CPU 2 proceeds to S18.

In the above-described embodiment, S10 to S19 are executed for each fuel cut period so as to determine a representative value Ipe. The processing of determining a representative value Ipe is not limited thereto. For example, the representative value Ipe may be determined for every other fuel cut period. However, determining the representative value Ipe for each fuel cut period is desirable, because a new correction coefficient Kp can be computed early in S27 or S30.

In the above-described embodiment, when a new correction coefficient Kp is computed, the weighted average Ipf or Ipg is used (S27 or S30). However, a new correction coefficient Kp may be computed using a single representative value Ipe. For example, the representative value Ipe is assumed to continuously fall outside the second range 82 four times (the representative values 331 to 334) as shown in FIG. 6. In such a case, in S30, the CPU 2 divides one of the four representative values 301 to 304 (e.g., the largest representative value 332) by the current correction coefficient Kp, and divides the reference value Ipa by the resultant value, to thereby compute a new correction coefficient Kp. In S27, the CPU 2 may compute a new correction coefficient Kp in the same manner.

In the above-described embodiment, the representative value Ipe is the weighted average Ipd of a plurality of corrected values Ipc. However, the representative value Ipe is not limited thereto. For example, the representative value Ipe may be one corrected value Ipc obtained in each fuel cut period, or the weighted average of a plurality of corrected values Ipc, excluding the largest one and the smallest one. Also, the representative value Ipe may be the weighted average of a plurality of output values Ipb obtained in each fuel cut period, or a single output value Ipb obtained in each fuel cut period.

Notably, in the case where the representative value Ipe is the output value Ipb or the weighted average thereof, the method of computing the correction coefficient Kp (S27 and S30), the first range 81, the second range 82, the third range 83, etc., differ from those employed in the above-described embodiment. For example, in S27 and S30, the CPU 2 computes a new correction coefficient Kp by dividing the reference value Ipa by the weighted average Ipf, Ipg of the representative values Ipe. Also, every time a new correction coefficient Kp is computed in S27, the CPU 2 updates the ranges 81, 82 and 83 to respective ranges which include the weighted average Ipf used for computation of the correction coefficient Kp. For example, the first range 81 is updated to "Ipf±1%", the second range 82 is updated to "Ipf±2%", and the third range 83 is updated to "Ipf±7.5%." Similarly, every time a new correction coefficient Kp is computed in S30, the CPU 2 updates the ranges 81, 82 and 83 to respective ranges which include the weighted average Ipg used for computation of the correction coefficient Kp. This modified embodiment provides the same effects as those provided by the above-described embodiment.

The embodiment has been described for an exemplary case where the first range 81 is "the reference value Ipa±1%" and the second range 82 is "the reference value Ipa±2%." However, the first and second ranges 81 and 82 are not limited thereto. For example, the respective centers of the first range 81 and the second range 82 may differ from the reference value Ipa. Also, the first range 81 may be "the reference value Ipa±0.8%" and the second range 82 may be "the reference value Ipa±1.1%." However, setting the width of the second range 82 to at least two times the width of the first range 81 is desirable, because the case where the mounted oxygen sensor 20 has deteriorated with time and the case where the mounted oxygen sensor 20 has been exchanged can be distinguished from each other more easily.

In the above-described embodiment, the reference value Ipa is a current output from the reference oxygen sensor when it is exposed to the ambient atmosphere (oxygen concentration: about 20.5%). However, the reference value Ipa is not limited thereto. For example, the reference value Ipa may be a value freely set in accordance with the design of the control apparatus.

The mounted oxygen sensor 20 is not limited to a two-cell-type air-fuel-ratio sensor, and may be a one-cell-type oxygen sensor. Alternatively, the mounted oxygen sensor 20 may be a sensor having an oxygen concentration detection function (e.g., an NOx sensor having an oxygen concentration detection function). Furthermore, the averaging processing for computing all the above-described weighted averages (the weighted average Ipd, etc.) is not limited to the weighted-averaging processing, and the averaging processing may be processing for obtaining the arithmetic average or moving average of relevant values.

The oxygen sensor control apparatus 10 functions as an ECU. The oxygen sensor control apparatus 10 is not necessarily required to function as an ECU. For example, the oxygen sensor control apparatus 10 is configured independently of the ECU. In such case, the fact that fuel cut has been started is reported from the ECU to the oxygen sensor control apparatus 10, and the oxygen sensor control apparatus 10 communicates the computed correction coefficient Kp to the ECU, whereby the correction coefficient Kp is updated.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2011-51801 filed Mar. 9, 2011, the disclosure of which is incorporated herein by reference in its entirety.

What is claimed is:

1. An oxygen sensor control apparatus which includes first storage means for storing a correction coefficient used for calibrating a relation between an output value of an oxygen sensor mounted to an exhaust pipe of an internal combustion engine and oxygen concentration of exhaust gas flowing through the exhaust pipe and which detects the oxygen concentration of the exhaust gas using the correction coefficient stored in the first storage means and the output value of the oxygen sensor, the oxygen sensor control apparatus comprising:

output value obtaining means for obtaining the output value of the oxygen sensor;

representative value determination means for determining a representative value from at least one output value obtained by the output value obtaining means in a fuel cut period during which supply of fuel to the internal combustion engine is stopped, the representative value representing output values in the fuel cut period;

first memorization control means for storing in second storage means the representative value in the fuel cut period determined by the representative value determination means;

first range judgment means for judging whether or not a latest representative value, which is the latest representative value stored in the second storage means by the first memorization control means, falls outside a predetermined first range;

second range judgment means for judging whether or not the latest representative value falls outside a predetermined second range, which contains the first range and is wider than the first range;

first representative value judging means for judging whether or not a first judgment count has reached a first number of times equal to or greater than two times, the first judgment count representing a number of times the latest representative value is continuously judged by the first range judgment means to fall outside the first range and the latest representative value is continuously judged by the second range judgment means not to fall outside the second range;

first computation means for computing a new value of the correction coefficient when the first representative value judging means judges that the first judgment count has reached the first number of times;

second representative value judging means for judging whether or not a second judgment count has reached a second number of times smaller than the first number of times, the second judgment count representing a number of times the latest representative value is continuously judged by the second range judgment means to fall outside the second range;

second computation means for computing a new value of the correction coefficient when the second representative value judging means judges that the second judgment count has reached the second number of times; and     second memorization control means for storing in the first storage means the new value of the correction coefficient computed by the first computation means or the second computation means.

2. The oxygen sensor control apparatus as claimed in claim 1, wherein the first number of times is three times or more; and the second number of times is two times or more but smaller than the first number of times.

3. The oxygen sensor control apparatus as claimed in claim 1, wherein the first computation means, which operates when the first representative value judging means judges that the first judgment count has reached the first number of times, computes a new value of the correction coefficient on the basis of the representative value stored in the second storage means and a preset reference value such that a corrected value obtained by multiplying the output value in the fuel cut period by the correction coefficient approaches the reference value; and     the second computation means, which operates when the second representative value judging means judges that the second judgment count has reached the second number of times, computes a new value of the correction coefficient on the basis of the representative value stored in the second storage means and the reference value such that the corrected value approaches the reference value.

4. The oxygen sensor control apparatus as claimed in claim 3, wherein the reference value falls within the first range and falls within the second range;

the representative value determination means determines a value which represents corrected values in the fuel cut period, as the representative value, on the basis of at least one of the corrected values each obtained by multiplying, by the correction coefficient, the output value obtained by the output value obtaining means in the fuel cut period;

the first computation means, which operates when the first representative value judging means judges that the first judgment count has reached the first number of times, computes a new value of the correction coefficient by dividing the reference value by a value obtained by dividing the representative value by a current value of the correction coefficient stored in the first storage means; and     the second computation means, which operates when the second representative value judging means judges that the second judgment count has reached the second number of times, computes the new value of the correction coefficient by dividing the reference value by the value obtained by dividing the representative value by the current value of the correction coefficient stored in the first storage means.

5. The oxygen sensor control apparatus as claimed in claim 3, wherein the first computation means, which operates when the first representative value judging means judges that the first judgment count has reached the first number of times, computes the correction coefficient on the basis of the reference value and a first average value, which is the average of at least two of representative values which fall outside the first range and fall within the second range; and     the second computation means, which operates when the second representative value judging means judges that the second judgment count has reached the second number of times, computes the correction coefficient on the basis of the reference value and a second average value, which is the average of at least two of representative values which fall outside the second range.

\* \* \* \* \*